United States Patent
Gruning et al.

(10) Patent No.: US 6,320,065 B1
(45) Date of Patent: Nov. 20, 2001

(54) FATTY ACID PARTIAL ESTERS OF POLYOLS

(75) Inventors: Burghard Gruning; Geoffrey Hills, both of Essen (DE)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 09/306,771

(22) Filed: May 7, 1999

(30) Foreign Application Priority Data

May 15, 1998 (DE) .............................................. 198 21 851

(51) Int. Cl.⁷ ............................. C07C 51/00; C07C 1/04; C11C 1/00; C11D 3/38; C12P 7/62
(52) U.S. Cl. ..................... 554/173; 554/170; 554/168; 554/171; 554/172; 554/229; 435/134; 435/135; 435/136; 435/137
(58) Field of Search ..................................... 554/173, 168, 554/170, 229, 171, 172, 277; 510/410, 470; 435/280, 135, 41, 134, 136, 137

(56) References Cited

U.S. PATENT DOCUMENTS 2,759,922 * 8/1956 Gibbons .............................. 260/210
5,674,830 * 10/1997 Brenkman et al. .................. 510/470

FOREIGN PATENT DOCUMENTS

| | | |
|---|---|---|
| 38 18 292 A1 | 12/1989 | (DE) . |
| 44 07 015 C2 | 9/1995 | (DE) . |
| 0 093 602 A2 | 11/1983 | (EP) . |
| 0 383 405 A1 | 8/1990 | (EP) . |
| 0 451 461 B1 | 10/1991 | (EP) . |
| 90/09451 | 8/1990 | (WO) . |

OTHER PUBLICATIONS

Osipow et al, Micro–Emulsion Process for the Preparation of Sucrose Esters, American Oil Chemists Society, vol. 44, May 1967.*

Rompp's Chemical Encyclopedia, 9th expanded edition (1990), pp. 1812–1913, entry: ELB.

* cited by examiner

Primary Examiner—Deborah D. Carr
(74) Attorney, Agent, or Firm—Scully, Scott, Murphy & Presser

(57) ABSTRACT

The invention relates to a process for the preparation of fatty acid partial esters of polyols, the fatty acid partial esters thus obtainable, and their use.

The fatty acid partial esters (I) of polyols having at least 4 C atoms, at least one primary and at least one secondary alcohol group of the starting polyols are obtained in a process, where in a first process step the polyols are reacted with a fatty acid or a fatty acid derivative to give a fatty acid partial ester (II) and in a second process step the fatty acid partial esters (II) obtained are subjected to a selective enzymatic cleavage of primary ester groups.

35 Claims, No Drawings

FATTY ACID PARTIAL ESTERS OF POLYOLS

FIELD OF THE INVENTION

The present invention relates to a process for the preparation of fatty acid partial esters of polyols, the fatty acid partial esters thus obtainable, and their use.

BACKGROUND OF THE INVENTION

German Patent Publication DE 38 18 292 A1 relates to a process for the preparation of fatty acid or hydroxy fatty acid esters of isopropylidene derivatives of a polyglycerol from fatty acid alkyl esters, mono- or polyhydroxy fatty acid alkyl esters having $C_6$–$C_{22}$ in the fatty acid component and $C_1$–$C_4$ in the ester components, which are reacted in an alkaline medium with one or more isopropylidene derivatives of a polyglycerol. The reaction is carried out at temperatures from 140 to 220° C. and in vacuo at 5 to 950 mbar. The $C_1$–$C_4$ alcohol formed in this reaction is removed by distillation and the reaction product is purified. Furthermore, the use of the fatty acid or hydroxy fatty acid esters of mono- and/or diisopropylidene derivatives of polyglycerol prepared in this way as intermediates for the preparation of nonionic surfactants, as solvents or solubilizers and for cosmetic preparations and skin care agents is described.

European Publicatin EP 0 383 405 A1 describes a process for the preparation of esters by reaction of a $C_7$–$C_{36}$ mono- or dicarboxylic acid and a $C_2$–$C_8$ monoalcohol in the presence of a lipase catalyst, the water of reaction being removed from the $C_2$–$C_8$ monoalcohol and water by azeotropic distillation of the mixture. In particular, the azeotropic distillation of the alcohol and the addition of the alcohol are carried out simultaneously at the same rate under reduced pressure. The process can be carried out in a one-pot system at a temperature below 80° C. The esterification and the azeotropic distillation can also be carried out in separate reaction vessels, in which higher temperatures and higher pressures can be used.

European Publication EP 0 451 461 B1 describes the use of mixtures of polyglycerol fatty acid esters as emulsifiers in cosmetic and pharmaceutical preparations. These are obtainable by partial esterification of polyglycerols with at least one saturated fatty acid having 12 to 22 C atoms or at least one unsaturated fatty acid having 16 to 22 C atoms, where the unsaturated fatty acid or fatty acid mixture employed can additionally contain up to 10% by weight of saturated fatty acids having 16 to 22 C atoms. The degree of esterification of the saturated or unsaturated fatty acids in the mixture is between 20 and 70%.

German Patent Publication DE 44 07 015 C2 relates to cosmetic and/or pharmaceutical preparations which, as emulsifiers, contain esters of palmitic acid with technical triglycerides with the proviso that the content of monoesters is 30 to 50% by weight.

European Publication EP 0 093 602 A2 describes a transesterification by means of a lipase enzyme system as a transesterification catalyst. In a continuous transesterification process, a fatty acid derivative, in particular a glycerol, which optionally contains free fatty acid, is brought into contact with an enzyme as a transesterification catalyst, which is preferably 1,3-selective and is immobilized on an inert particulate carrier. The catalyst is packed in a solid bed and remains in contact with the reaction mixture for less than 2 hours. The process is particularly suitable for the preparation of POSt- and StOSt-rich fats, which are suitable as a cocoa butter substitute (P here stands for palmitate, O for oleate and St for stearate).

International Publication WO 90/09451 describes fatty acid esters of methyl glycosides which are obtained by reaction of a fatty acid or of a fatty acid ester with a methyl glycoside in the presence of an enzyme catalyst, in particular of a lipase. The resulting fatty acid esters are preferably monoesters. Methyl glycoside fatty acid esters can be employed as surface-active agents in cleansing agents or cosmetic agents.

SUMMARY OF THE INVENTION

In contrast, the object of the present invention consists, in particular in the provision of fatty acid partial esters of polyols having at least 4 C atoms, at least one primary and at least one secondary alcohol group in the starting substances, in increasing the content of ester groups on the secondary alcohol groups compared to the prior art. Moreover, the object of the present invention consists in making available improved oil-in-water emulsifiers, in particular compounds having a hydrophobic and a hydrophilic entity, which customarily have HLBs of more than 10. According to Römpp's Chemical Encyclopedia, 9th expanded edition (1990), pp. 1812–1913, entry: HLB system, the HLB is a measure introduced by Griffin (1950) for the water or oil solubility of mainly nonionic surfactants and the stability of emulsions, for example in cosmetics. Another measure of the emulsion stability is the zeta potential, which has a maximum in the optimum HLB range. Experimentally, the HLB can be determined, for example, by the phenol titration method, in which the surfactant solution is treated with a 5% strength phenol solution until turbidity. The HLB can furthermore be determined (gas-) chromatographically, by determination of the dielectric constant or colorimetrically. For the calculation of HLBs: for fatty acid esters of polyhydric alcohols, the relationship $HLB = 20(1 - VZ/SZ)$ applies, where VZ is the hydrolysis number and SZ is the acid number of the ester. For ethoxylates and their esters, in which the VZ can only be determined with difficulty, the formula $HLB = (E+P)/5$ applies, where E is the number of ethylene oxide units and P is the content of polyhydric alcohols (data in % by weight) in the molecule. It may be pointed out that this calculation method cannot be used for polypropylene glycol ethers and anionic surfactants. The HLB of a surfactant or emulsifier mixture can be calculated additively from the values of its constituents. The scale here as a rule extends from 1 to 20, or rarely to 40. Substances having a low HLB (<10) are in general good W/O emulsifiers, while more hydrophilic surfactants having a higher HLB act as O/W emulsifiers.

Nonionic emulsifiers (sodium lauryl ether sulfate-free) and polyethylene glycol-free emulsifiers, which are preferably employed in the cosmetic field, are commercially obtainable. Corresponding polyglycerol esters I are made available with the aid of the present invention.

Triglycerol monoisostearates are disclosed in the abovementioned DE 38 18 292 A1 which carry the ester group in the center position. These are prepared by protective group chemical reaction (isopropylidene derivatives) at both ends of the glycerol groups. Compared with this, it was an object of the present invention to simplify the process for the preparation of the abovementioned substances.

Customary polyglycerol fatty acid esters II which are prepared by chemical esterification have a low hydrophilicity and do not form stable oil-in-water emulsions.

DETAILED DESCRIPTION OF THE INVENTION

The abovementioned objects of the present invention are achieved in a first embodiment by a process for the preparation of fatty acid partial esters of polyols having at least 4 C atoms, at least one primary and at least one secondary alcohol group of the starting polyols, where in a first process step the polyols are reacted with a fatty acid or a fatty acid derivative to give a fatty acid partial ester and in a second process step the fatty acid partial esters obtained are subjected to a selective enzymatic cleavage of primary ester groups.

With the aid of the present invention, it is possible to markedly simplify the preparation of fatty acid partial esters from polyols having at least 4 C atoms, at least one primary and at least one secondary alcohol group of the starting substances, compared with the prior art. In particular, protective group chemistry is not necessary. Moreover, it is possible to carry out the process according to the invention entirely without solvent. The products thus obtainable are better suited as oil-in-water emulsifiers than products which are prepared without the enzymatic reaction. Thus, for example, polyglycerol esters having a high content of monoesters (more than 50%) are obtainable which are mainly secondary esters.

Owing to the nonuse of protective group technology, fewer by-products are obtained than in the prior art. The products are moreover purer than those known in the prior art, since these contain no catalyst or solvent residues. Owing to the regiospecific reaction of the enzymes, products are obtainable whose specific compositions were not known in the prior art. The fatty acid partial esters of polyols obtainable according to the invention are suitable for particular applications, for example as oil-in-water emulsifiers in emulsions having a high salt content, as solubilizing agents or as a surface-active substance in cosmetic, pharmaceutical and cleansing preparations.

Particularly preferably, polyols were employed which have at least 4 hydroxyl groups.

In a further preferred embodiment of the present invention, the polyols are selected from carbohydrates, in particular monosaccharides, oligosaccharides, polyglycerols and alkyl glycosides having 1 to 20 C atoms in the alkyl radical. The selection of the carbohydrates is not restricted here, so monosaccharides are preferably employed which are selected from erythrose, threose, arabinose, ribose, xylose, glucose, mannose, galactose, fructose, sorbose, sorbitol, manitol and dulcitol. In an analogous manner to the monosaccharides, the oligosaccharides are selected from disaccharides, in particular sucrose, trehalose, lactose, maltose and cellobiose, and the trisaccharides, in particular raffinose. Particularly preferably, the sugar alcohols are selected from sorbitol, xylitol or erythritol, while the alkyl glycosides preferably include methyl glycoside.

As is known, polyglycerols are ethers of glycerol, which are prepared industrially, for example, by base-catalyzed condensation of glycerol. These polyglycerols also occur as by-products of epichlorohydrin hydrolysis. The separation and isolation of the individual polyglycerols is possible by means of treatment with various agents. As the simplest condensation product, diglycerol and its higher oligomers are known as synthetic block-building substances, which are employed for a number of products. Fatty acid esters of these polyglycerols are thus also known in principle in the prior art. Within the meaning of the present invention, technical mixtures of polyglycerols are particularly preferably employed which customarily contain diglycerol, triglycerol, tetraglycerol and pentaglycerol.

The fatty acids and fatty acid derivatives to be preferably employed within the meaning of the present invention are derived from straight-chain or branched, saturated, mono- or polyunsaturated fatty acid radicals having 6 to 24 C atoms, in particular 12 to 18 C atoms. In this context, stearic acid and palmitic acid are particularly preferred, which yield solid emulsifiers with polyglycerols within the meaning of the present invention. If, for example, isostearic acid or oleic acid is employed as a reaction component, liquid emulsifiers are obtained, in particular on reaction with polyglycerols.

Fatty acid derivatives which can be employed are all customary derivatives which enter into esterification reactions. Accordingly, the fatty acid derivatives are particularly preferably selected from fatty acid halides, fatty acid anhydrides and fatty acid alkyl esters having 1 to 4 C atoms in the alcohol radical.

Within the meaning of the present invention, the quantitative ratio of fatty acid or fatty acid derivative to polyol can be set according to generally customary ratios. It is particularly preferred within the meaning of the present invention to set the quantitative ratio of fatty acid derivatives to polyols in the ratio from 0.1 to 5:1, in particular 0.5 to 3:1.

In principle, the first stage of the process, which is known per se from the prior art, is realized by carrying out the reaction at 110 to 300° C., in particular 240 to 280° C., for the reaction of polyglycerols in the course of 2 to 12 hours, in particular 3 to 5 hours, in particular under inert gas, for example nitrogen, with distillative removal of the resulting water or alcohol, if appropriate in the presence of solvent and/or of an acidic or basic catalyst. It is particularly preferred within the meaning of the present invention to carry out the esterification reaction of the first process step in the presence of a basic catalyst, such as, for example, of a fatty acid soap, in particular calcium stearate, in the presence of $K_2CO_3$ or $Na_2CO_3$. The reaction of other polyols, for example sugar alcohols, as a rule necessitates low reaction temperatures because of the instability of the alcohols, which at higher temperatures often undergo ring-closure reactions. For example, in the case of the reaction of sorbitol the temperature range from 110 to 150° C. is preferred.

The second stage of the reaction, namely the selective cleavage of the primary ester groups, is carried out by means of an enzymatic reaction, such that the product obtained preferably contains primary hydroxyl groups and secondary fatty acid esters and also a relatively low number of secondary hydroxyl groups. This is achieved by hydrolysis/alcoholysis of the fatty acid partial ester obtained in the first process step by a hydrolysis or transesterification, if appropriate in customary solvents for enzymatic reactions or suspending media which comprise water or short-chain alcohols, in particular having 1 to 8 C atoms. The present invention also contemplates alkanes, ethers, ketones, and mxixtures thereof as solvents or suspending media.

Enzymatic cleavage by means of enzymes, in particular immobilized enzymes, is in particular carried out using those enzymes which are selected from lipases, esterases or proteases, in particular lipases having defined enzyme catalysis reactivity for ester bonds, in particular hydrolysis, synthesis and/or exchange of ester bonds. Lipases of this type are described in WO 90/09451 mentioned at the outset. Moreover, the product Novozym®435 from Novo Nordisk is known as an immobilized and commercially obtainable thermostable lipase system. This enzyme is particularly preferably employed within the meaning of the present invention.

The amount of the enzyme catalyst is 0.1 to 10% by weight, preferably 1 to 5% by weight. The reaction time depends on the amount and the activity of the enzyme catalyst used and is, for example, up to 48 hours, preferably up to 24 hours.

The production system can be characterized either by a stirred tank reactor or a packed bed reactor.

In the stirred tank reactor, the enzyme catalyst can be separated off after reaction is complete by means of suitable measures such as filtration or decantation and, if appropriate, reused a number of times. The packed bed reactor is equipped with immobilized enzymes, the reaction mixture being pumped through the column packed with catalyst. The reaction mixture can be pumped through the column continuously, it being possible to control the residence time and thus the desired conversion by the flow rate. It is also possible to pump the reaction mixture through the column in circulation until the reaction is finished.

Using an enzyme immobilized on a carrier, it is also possible to carry out the reaction in a fluidized bed.

With the aid of the process defined at the outset, fatty acid partial esters of polyols are obtainable which have an increased content of fatty acids esterified with secondary alcohols compared with customary esterification. This advantage makes itself particularly apparent in the case of fatty acid partial esters of polyglycerols which are obtainable with the aid of the present invention having a content of monoesters of more than 50 to 90% by weight.

The fatty acid partial esters of polyols, as defined, are particularly preferably employed within the meaning of the present invention as emulsifiers in oil-in-water emulsions.

The following working examples represent preferred realizations of the present invention, but are not suitable for restricting the invention thereto.

EXAMPLE 1

191 g of commercially available polyglycerol T (manufacturer Solvay), which contains at least 40% by weight of tetraglycerol, at most 50% by weight of di-, tri- and pentaglycerol and at most 20% by weight of hexa-, hepta- and octaglycerol, were heated at 260° C. for 2.5 hours with 160 g of oleic acid and 0.7 g of calcium stearate with nitrogen purging in order to form a polyglycerol (mono)oleate. An equal amount of isopropanol was added to this product and 1% by weight of enzyme catalyst Novozym®435 was added at 60° C. After 22 hours, the catalyst was filtered off and the residual isopropanol was removed by distillation. The compositions of the partial esters before II and after the enzymatic I reaction are indicated in Table 1.

The compositions are expressed in percentages by weight, and were obtained by gel permeation chromatography.

EXAMPLE 2

250 g of polyglycerol T were heated with 207.5 g of stearic acid at 260° C. under nitrogen purging for 4 hours. The polyglycerol esters obtained were treated with an equal amount of isopropanol, after which 1% by weight of enzyme catalyst (Novozym® 435) was added at 60° C. After reaction for 16 hours, the catalyst was filtered off and the isopropanol was removed by distillation. The compositions of the esterified products before and after the enzymatic reaction are shown in Table 1.

EXAMPLE 3

A mixture of sorbitol (24.2 g), methyl palmitate (108.2 g), sodium palmitate (7.35 g) and $Na_2CO_3$ (0.93 g) was stirred and heated to 150° Cc with $N_2$ purging. After 12 h, the reaction mixture was cooled. The yield was 92% of sorbitol palmitate II with the composition of the sorbitol esters after GPC analysis: monoester 9%, diester 26%, triester 36% and tetraester +ff 29%.

10 g of this product were dissolved in 20 g of 1-hexanol at 60° C. and 2 g of enzyme catalyst (Novozym® 435) were added. After 20 h, the sorbitol palmitate had the composition which is shown in Table 1. Since hexyl palmitate and the monoesters had the same $R_f$ values in the solvent, it was not possible to separate these.

TABLE 1

Composition of the polyglycerol esters before and after I of the enzymatic treatment (% by weight)

| Product | Mono ester | Diester | Triester +ff | Tetraester +ff | Isopropyl ester |
|---|---|---|---|---|---|
| Example 1 | | | | | |
| Polyglycerol (mono)oleate | 40 | 35 | 25 | — | — |
| After the enzymatic reaction I | 32 | 14 | 8 | — | 46 |
| New polyglycerol ester content | 59 | 26 | 15 | — | — |
| Example 2 | | | | | |
| Polyglycerol (mono)stearate | 39 | 33 | 28 | — | — |
| After the enzymatic reaction I | 36 | 15 | 14 | — | 35 |
| New polyglycerol ester content | 55 | 23 | 22 | — | — |
| Example 3 | | | | | |
| sorbitol palmitate ester | 9 | 26 | 36* | 29 | — |
| After the enzymatic reaction I | 37** | 16 | 24 | 23 | — |

*only triester on its own
**sum of monoester and hexyl palmitate

EXAMPLE 4

Use of O/W emulsifier Polyglycerol T stearate from Example 2, chemically esterified (PGTS) II and enzymatically modified I in comparison with triglycerol monostearate III synthesized by means of protective group chemistry were in each case introduced into an

| O/W emulsion of | paraffin oil | 19% |
|---|---|---|
| | TEGIN M | 3.0% |
| | Stearyl alcohol | 1.0% |
| | K stearate | 0.03% |
| + emulsifier | (I) $PGTS_{enz}$ (corresponds to 1.4% of PG ester) | 2.0% |
| | (II) PGTS | 1.4% |
| | (III) TGMS | 1.4% |
| | water | to 100, |

The following properties were determined for the emulsions I, II and III:

| Emulsion | I | II | III |
|---|---|---|---|
| Degree of dispersion | finely disperse | coarsely disperse | coarsely disperse |
| Viscosity (Pas) | 36 | 45 | 8 |
| measured at room temperature in a Brookfield viscometer with an RVT Helipath spindle to 140 pm | | | |
| Stability at: | | (after 2 months) | |
| Room temperature | stable | stable | unstable |
| 40° C. | stable | stable | unstable |
| 45° C. | stable | unstable | unstable |
| Freezing/thawing cycles | no separation | medium separation | strong separation |
| by cooling to −15° C. and warming to room temperature five times | | | |

While the invention has been particularly shown and described with respect to preferred embodiments thereof, it will be understood by those skilled in the art that the foregoing and other changes in form and details may be made therein without departing from the spirit and scope of the invention.

What is claimed is:

1. A process for the preparation of fatty acid partial esters of polyols having at least 4 carbon atoms, at least one primary and at least one secondary alcohol of initial polyols, comprising reacting polyols with a fatty acid or a fatty acid derivative to provide a fatty acid partial ester and subjecting said fatty acid partial ester to a selective enzymatic reaction wherein primary ester groups of said fatty acid partial ester are cleaved.

2. The process as claimed in claim 1, wherein said polyols are employed which have at least 4 hydroxyl groups.

3. The process as claimed in claim 1, wherein said polyols are selected from the group consisting of carbohydrates, oligosaccharides, polyglycerols, sugar alcohols and alkyl glucosides having 1 to 20 carbon atoms in the alkyl radical.

4. The process according to claim 3, wherein said carbohydrates are monosaccharides.

5. The process as claimed in claim 4, wherein said monosaccharides are selected from the group consisting of erythrose, threose, arabinose, ribose, xylose, glucose, mannose, galactose, fructose, sorbose, sorbitol, mannitol, xylitol, erythritol and dulcitol.

6. The process as claimed in claim 3, wherein said oligosaccharides are selected from the group consisting of disaccharides, trehalose, lactose, maltose and cellobiose.

7. The process as claimed in claim 6, wherein said disaccharides are sucrose.

8. The process as claimed in claim 3, wherein said alkyl glucosides are selected from the group consisting of methyl glucoside, ethyl glucoside and mixtures thereof.

9. The process as claimed in claim 3, wherein said polyglycerols contain diglycerol, triglycerol, tetraglycerol, pentaglycerol or mixtures thereof.

10. The process as claimed in claim 1, wherein said fatty acids have straight-chain or branched saturated, mono- or polyunsaturated fatty acid radicals having 6–24 carbon atoms.

11. The process as claimed in claim 10, wherein said fatty acid radicals have 12 to 18 carbon atoms.

12. The process as claimed in claim 1, wherein said fatty acid derivatives have straight-chain or branched, saturated, mono- or polyunsaturated fatty acid radicals having 6–24 carbon atoms.

13. The process as claimed in claim 12, wherein said fatty acid derivatives are selected from the group consisting of fatty acid halides, fatty acid anhydrides, fatty acid alkyl esters having 1–4 carbon atoms in the alcohol radical, and mixtures thereof.

14. The process as claimed in claim 1, wherein the quantitative ratio of fatty acid to polyol is from 0.1:1 to 5:1.

15. The process as claimed in claim 14, wherein the quantitative ratio of fatty acid to polyol is from 0.5:1 to 3:1.

16. The process as claimed in claim 1, wherein the quantitative ratio of fatty acid derivative to polyol is from 0.1:1 to 5:1.

17. The process as claimed in claim 16, wherein the quantitative ratio of fatty acid derivative to polyol is from 0.5:1 to 3:1.

18. The process as claimed in claim 1, wherein the quantitative ratio of fatty acid and fatty acid derivate to polyol is from 0.1:1 to 5:1.

19. The process as claimed in claim 18, wherein the quantitative ratio of fatty acid and fatty acid derivative to polyol is from 0.5:1 to 3:1.

20. The process as claimed in claim 1, wherein said first process step is carried out at a temperature of from about 110° to about 300° C., and for a period of about 2 to about 12 hours, under inert gas, with distillative removal of any resulting water or alcohol.

21. The process as claimed in claim 20, wherein said first process step is carried out at a temperature of from about 240° to about 280° C.

22. The process as claimed in claim 20, wherein said first process step is carried out for a period of from about 3 to about 5 hours.

23. The process as claimed in claim 20, wherein said inert gas is nitrogen.

24. The process as claimed in claim 20, wherein said first process step is carried out in the further presence of a solvent.

25. The process as claimed in claim 20, wherein said first process step is carried out in the further presence of a catalyst.

26. The process as claimed in claim 20, wherein said first process step is carried out in the further presence of a solvent and a catalyst.

27. The process as claimed in claim 1, wherein said second process step is carried out in a solvent or suspending medium which comprises water or short-chain alcohols having 1 to 8 carbon atoms, alkanes, ethers, ketones, and mixtures thereof.

28. The process as claimed in claim 27, wherein said alkane is hexane.

29. The process as claimed in claim 27, wherein said ether is diethyl ether.

30. The process as claimed in claim 27, wherein said ketone is acetone.

31. The process as claimed in claim 1, wherein said second process step is carried out by means of enzymes.

32. The process as claimed in claim 31, wherein said enzymes are immobilized enzymes, and are selected from the group consisting of lipases, esterases and proteases.

33. A fatty acid partial ester,(I) of polyols obtained by the process of claim 11.

34. The fatty acid partial ester (I) of polyglycerols as claimed in claim 33 having a content of monoesters of more than 50 to 90% by weight.

35. An emulsifier in oil-in-water emulsions comprising the fatty acid partial ester (I) of polyols of claim 33.

* * * * *